US008795299B2

(12) United States Patent
De Winter

(10) Patent No.: US 8,795,299 B2
(45) Date of Patent: Aug. 5, 2014

(54) ANCHORING SCREW DEVICE

(76) Inventor: Erwin De Winter, Mortsel (BE)

( * ) Notice: Subject to any disclaimer, the term of this patent is extended or adjusted under 35 U.S.C. 154(b) by 376 days.

(21) Appl. No.: 12/556,114

(22) Filed: Sep. 9, 2009

(65) Prior Publication Data

US 2009/0326471 A1   Dec. 31, 2009

Related U.S. Application Data

(63) Continuation of application No. 10/554,947, filed as application No. PCT/BE03/00120 on Jul. 7, 2003, now abandoned.

(30) Foreign Application Priority Data

Apr. 28, 2003  (WO) .................. PCT/BE03/00074

(51) Int. Cl.
*A61B 17/08* (2006.01)
(52) U.S. Cl.
USPC .......................................... 606/151; 606/153
(58) Field of Classification Search
USPC ............ 604/174, 164.11, 533, 164.04; 606/8, 606/151–158
See application file for complete search history.

(56) References Cited

U.S. PATENT DOCUMENTS

| 5,671,773 | A | | 9/1997 | Park |
| 5,755,697 | A | | 5/1998 | Jones et al. |
| 5,810,851 | A | * | 9/1998 | Yoon ............................ 606/148 |
| 5,810,882 | A | | 9/1998 | Bolduc et al. |
| 5,891,100 | A | | 4/1999 | Fleckenstein |
| 6,113,611 | A | * | 9/2000 | Allen et al. .................... 606/151 |
| 6,132,438 | A | | 10/2000 | Fleischman et al. |
| 6,171,320 | B1 | * | 1/2001 | Monassevitch ............... 606/151 |
| 6,210,397 | B1 | * | 4/2001 | Aboul-Hosn et al. ........ 604/533 |
| 6,379,366 | B1 | | 4/2002 | Fleischman et al. |
| 6,709,425 | B2 | * | 3/2004 | Gambale et al. .............. 604/500 |
| 6,960,217 | B2 | * | 11/2005 | Bolduc .......................... 606/108 |
| 2002/0011636 | A1 | | 8/2002 | Fleischman et al. |
| 2006/0025790 | A1 | | 2/2006 | de Winter |
| 2006/0241659 | A1 | | 10/2006 | Tulleken |
| 2006/0253080 | A1 | | 11/2006 | Tulleken |
| 2006/0259050 | A1 | | 11/2006 | de Winter |

FOREIGN PATENT DOCUMENTS

DE         198 26 078 C1      8/1999

OTHER PUBLICATIONS

Nov. 5, 2008 Office Action from co-pending U.S. Appl. No. 10/554,986.

* cited by examiner

*Primary Examiner* — Matthew F Desanto
(74) *Attorney, Agent, or Firm* — Sughrue Mion, PLLC

(57) ABSTRACT

The present invention, the ASD, is a mechanical device for anchoring hollow tube-like structures in the human body, such as blood vessels and ureters. It facilates positioning needles or catheters in blood vessels and it prevents those from dropping out of the vessel or from "wandering off" in the vessel. The ASD can be used in every interventional medical situation for diagnostic or therapeutic purposes. The ASD is very easy to fix onto the vessel wall. Screwing is a fast technique saving operating time and requiring only basic microsurgical skills. The manufacturing is easy. It should be understood that the foregoing is illustrative and nor limiting, and that modifications may be made by those skilled in the art, without departing from the scope of the invention.

25 Claims, 2 Drawing Sheets

ANCHORING SCREW DEVICE

FIELD

The present invention relates to anchoring a SCREW-DEVICE onto a tube-like structure, for example a blood vessel, in such a way (1) that a needle or a catheter can be passed safely into the hollow structure and (2) that this needle or catheter can be positioned firmly in the vessel so that it cannot slip out or be displaced (i.e., be carried away by the fluid in the vessel).

BACKGROUND ART

In many interventional medical procedures we want to reach hollow structures like a blood vessel or a ureter. During these procedures we want to place a catheter or a needle into the hollow structure to have access to it, mostly for therapeutic reasons such as the administration of medication, the placing of a stent or a coil, dilatation and so on. Sometimes access to the aforementioned hollow structures is necessary for diagnostic purposes.

The firm and stable fixation of a catheter into the wall of a hollow structure is essential since the catheter should under no circumstances fall out of the vessel or 'wander off' into the vessel. In the human body some hollow structure are embedded in surrounding tissue which enables the catheter to stay in place. This is the case, for example, with the blood vessels in a limb. It is completely different in the thorax, skull, or abdomen, where hollow structure are surrounded by less connective tissue and a catheter can easy slip out or be displaced. To prevent this, the catheter has to be fixated by suturing it to the wall of the vessel, but this is difficult and time consuming.

The present invention, the ASD, can easily be screwed onto the vessel-wall, where it gives a maximum stability and support for the catheter, which can then safely be inserted into the vessel.

Interventional fields include diagnostic procedures that involve the implantation of a catheter or needle; and therapeutic procedures that involve interventions (such as placing a catheter for medication) or that involve surgical operations, laparascopy, possibly in combination with endoscopic procedures.

SUMMARY OF INVENTION

The invention makes it possible to anchor a hollow structure, like a blood vessel, easily and quickly. More specifically, the ASD allows the physician dealing with medical intervention to make a stable and safe connection with a hollow structure in such a way that a catheter can be firmly positioned without any need for time consuming suturing.

DETAILED DESCRIPTION OF THE INVENTION

The ASD 1 takes the form of a hollow screw, with an ending that is not—as in the regular screw—a point, but one full spiral winding (360 degrees). The end of the winding is sharp and round, i.e., it is non-cutting but it is capable of perforating the wall of the hollow tube-like structure in which it is screwed. The sharp, round point 10 is bent inwardly and downwardlly in an angle of 10 to 20 degrees ($\alpha$) (see FIG. 1a). Alternatively, the sharp, round, non-cutting point 100 may bend downwardly in an angle of 90 degrees ($\alpha$) (see figure 1b). In this case, the end resembles a cork-screw, but the end is not situated in the middle of the final winding but on the periphery.

Figure 1A:
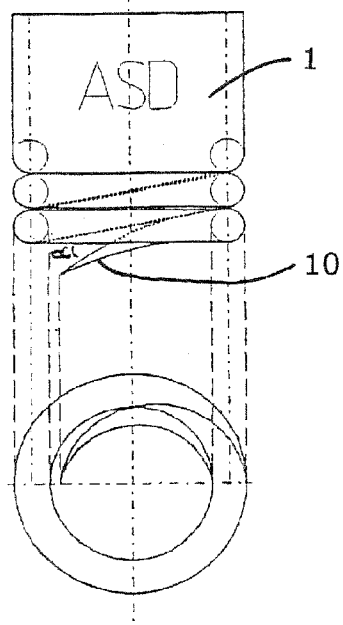
FIG. 1a and 1b illustrate two embodiments of the ASD.
Figure 1B:
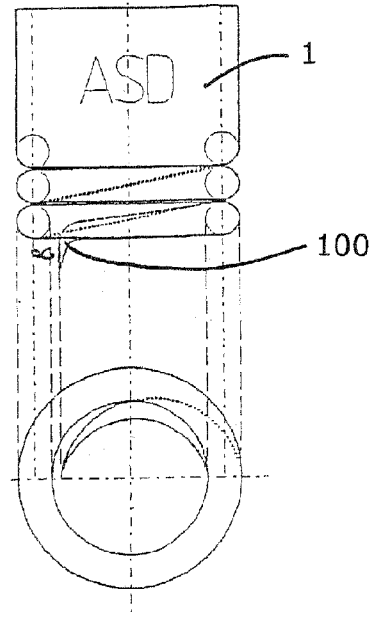
Figure 1C:
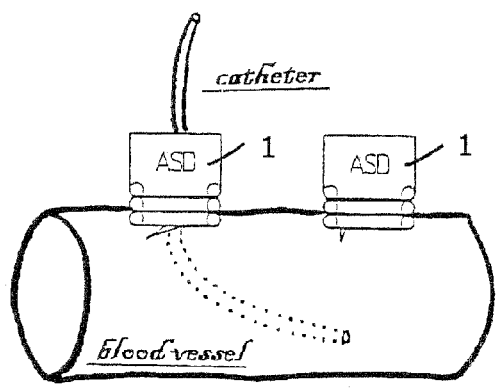
FIG. 1c illustrates the ASD inserted onto the wall.
Figure 2:
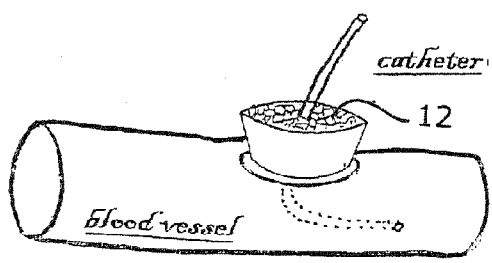
FIG. 2 illustrates the ASD filled with thrombostatic or haemostatic material.

The ASD 1 shown in FIG. 2 is the same as mentioned in FIGS. 1a-1c, but with the body of the screw filled with thrombostatic or haemostatic material 12 that functions as a sponge against leakage of the vessel after the catheter has been removed.

FIGS. 3a-3d illustrate an ASD 200 with a removable head. This device consists of two basic parts: first, the removable head 14 with applicator 16 (i.e., a long, thin shaft with a handle 18 used to drill the head into the vessel wall) and second, a hollow ASD 20 with a hollow screw of three windings, which remains in place (i.e., in the vessel wall).

Figure 3A:
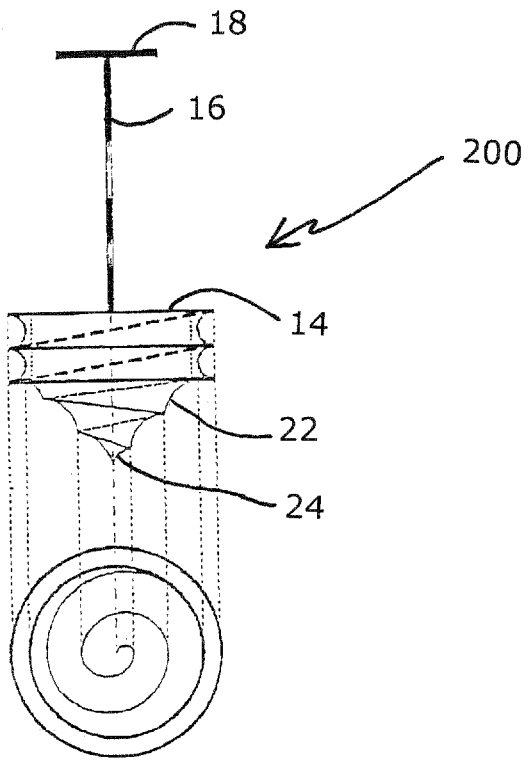
FIG. 3a illustrates a lateral view of an ASD with a removable head.
Figure 3B:
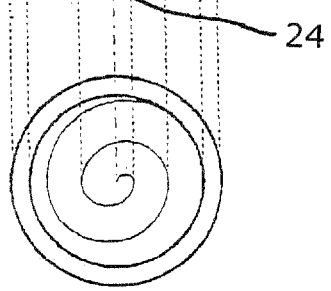
FIG. 3b illustrates a top view of the ASD of FIG. 3a with a removable head.
Figure 3C:
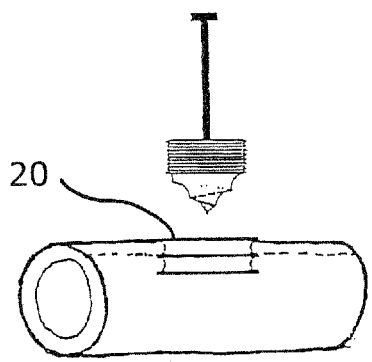
FIG. 3c illustrates an in situ view of the ASD of FIGS. 3a and 3b, with the removable head as positioned into the wall.

The removable head 14 consists of two windings, and ends in the form of a corkscrew 22 (see FIGS. 3a, 3b). This is, again, a round, sharp, non-cutting point 24. The head forms one whole with the applicator. Once the head 14 is in place (i.e., in the middle of the vessel wall) (see FIG. 3c), it is removed, together with the applicator 16, from the rest of the ASD that stays within the vessel wall.

Figure 3D:
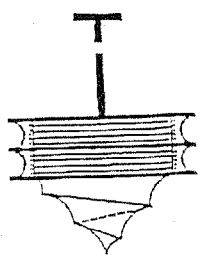
FIG. 3d illustrates the ASD with removable head of FIGS. 3a-3c, showing a view of the way in which the removable head is attached to the body of the ASD.

The second part is the body of the ASD 20 is shown in FIG. 3d. It consists of three hollow windings attached to the head by means of internal, anti-clockwise windings. Every winding is wider than the previous one, thus expanding the vessel wall. The opening in the wall is made by the head in a non-occlusive way, i. e. the receptor vessel need not be temporarily occluded.

Depending on the sort of hollow structure, like a blood-vessel, the diameter of ASD may vary from 1 millimeter to 2 centimeters, or even more.

The ASD is made of inox material, or titanium, or super-elastic materials such as nitinol, or synthetic materials, or even resorbable materials.

Depending on the diameter of the blood-vessel, the material may vary from 0.1 mm to any desirable thickness.

The elasticity of the ASD depends on the material used.

The ASD is screwed one turn of 360 degrees into the receptor wall. This ensures a stable fixation on the wall. A needle or a catheter is then inserted through the ASD into the wall, and is fixed onto the ASD so that it cannot slip out of the vessel or 'wander off' in to the vessel.

The screw device can be manufactured commercially and be employed to anastomose two vessels of different or identical sizes. It can be used in all domains of vascular surgery, heart surgery, and neurosurgery.

What is claimed is:
1. Surgical screw-device configured to be anchored onto a wall of a tube-like structure inside the human body, the screw-device comprising a hollow screw having a longitudinal axis passing through the hollow of the screw with a plurality of windings coaxially aligned with each other with respect to the longitudinal axis, wherein at least two of the windings of the hollow screw are loose from each other in an axial direction of the hollow screw along the longitudinal axis, the at least two adjacent windings anchor and stably fix the wall of the tube-like structure between them without the need for occluding the tube-like structure by respectively retaining the inner and outer surfaces of the wall between the two adjacent windings, a front winding of said windings has a sharp perforating end rounded to a point in a conical manner, for perforating the wall of the tube-like structure in such a way that passage of the windings of the hollow screw through the wall of the tube-like structure by screwing is enabled to anchor the screw-device to the wall of the tube-like structure, and the two adjacent windings remain coaxially aligned with each other when the screw device is anchored to the wall, wherein the screw-device further comprises a hollow structure fixed onto the windings of said hollow screw.

2. Surgical screw-device according to claim 1, wherein the sharp perforating end is rounded to a point for perforating the wall of the tube-like structure.

3. Surgical screw-device according to claim 2, wherein the sharp perforating end is bent inwardly and downwardly in an angle of 10 to 20 degrees with respect to the other windings.

4. Surgical screw-device according to claim 2, wherein the sharp perforating end is bent downwardly in an angle of 90 degrees with respect to the other windings.

5. Surgical screw-device according to claim 1, wherein the hollow screw is filled with thrombostatic or haemostatic material.

6. Surgical screw-device according to claim 1, wherein the hollow screw is made of inox material, or titanium, or super-elastic materials or synthetic materials, or resorbable materials.

7. Surgical screw-device according to claim 1, wherein the tube-like structure is a blood vessel or a ureter.

8. A surgical apparatus for treating a patient, comprising:
a screw-device configured to be anchored onto a wall of a tube-like structure inside the human body, the screw-device comprising a hollow screw having a longitudinal axis passing through the hollow of the screw with windings coaxially aligned with each other with respect to the longitudinal axis, and
a means for treating the patient, fixed on the screw-device, wherein:
the windings of the hollow screw are loose from each other in an axial direction of the hollow screw along the longitudinal axis and are configured to stably fix the wall of the tube-like structure between them without the need for occluding the tube-like structure by respectively retaining the inner and outer surfaces of the wall between the two adjacent windings,
a front winding of said windings has a sharp perforating end rounded to a point in a conical manner, for perforating the wall of the tube-like structure in such a way that passage of the windings of the hollow screw through the wall of the tube-like structure by screwing is enabled to anchor the screw-device to the wall of the tube-like structure, and
the two adjacent windings remain coaxially aligned with each other when the screw device is anchored to the wall.

9. The surgical apparatus according to claim 8, wherein the means for treating the patient comprises a catheter that projects in the tube-like structure through the screw-device.

10. Surgical screw-device according to claim 8, wherein the tube-like structure is a blood vessel or a ureter.

11. Surgical screw-device configured to be anchored onto a wall of a tube-like structure inside the human body, the screw-device comprising a hollow screw having a longitudinal axis through the hollow of the screw with a plurality of windings coaxially aligned with each other with respect to the longitudinal axis, wherein a front winding of said plurality of windings has a sharp perforating end rounded to a point in a conical manner for perforating the wall of the tube-like structure in such a way that passage of the windings of the hollow screw by screwing is enabled to anchor the screw-device to the wall of the tube-like structure;

the front winding and at least one subsequent winding of the plurality of windings are loose from each other in axial direction of the hollow screw along the longitudinal axis and are configured to anchor and stably fix the wall of the tube-like structure between them without the need for occluding the tube-like structure by respectively retaining the inner and outer surfaces of the wall between two adjacent windings;

the hollow screw is fully open at a rear winding and inwardly from the plurality of windings, such that insertion of a needle or catheter through the screw-device into the wall of the tube-like structure is not obstructed; and the two adjacent windings remain coaxially aligned with each other when the screw device is anchored to the wall, wherein said sharp perforating end is bent downwardly in an angle of 90 degrees with respect to the other windings.

12. Surgical screw-device according to claim 11, wherein said front winding is a full spiral winding of 360 degrees.

13. Surgical screw-device according to claim 11, wherein the tube-like structure is a blood vessel or a ureter.

14. Surgical screw-device according to claim 11, wherein said sharp perforating end is rounded to a point for making a round perforation in the wall of the tube-like structure and subsequently expanding said round perforation without cutting.

15. Surgical screw-device according to claim 11, wherein said sharp perforating end is bent inwardly and downwardly in an angle of 10 to 20 degrees with respect to the other windings.

16. Surgical screw-device according to claim 11, wherein the screw-device further comprises a hollow structure, such as a vessel or a catheter, fixed onto the windings of said hollow screw.

17. Surgical screw-device according to claim 11, wherein the screw-device comprises a hollow tube which is attached to a rear winding of said plurality of windings and is filled with thrombostatic or haemostatic material that functions as a sponge against leakage.

18. Surgical screw-device according to claim 11, wherein the hollow screw is made of inox material, or titanium, or super-elastic materials, or synthetic materials, or resorbable materials.

19. A method of fixing a means for treating the patient to a tube-like structure inside the human body, comprising:
providing a hollow screw having a longitudinal axis passing through the hollow of the screw with a plurality of windings coaxially aligned with each other with respect to the longitudinal axis, at least two of the windings of the hollow screw being loose from each other in an axial direction of the hollow screw along the longitudinal axis, and a front winding of said windings having a perforating end;

attaching the hollow screw to a wall of the tube-like structure by perforating the wall with the sharp perforating end of the front winding and rotating the hollow screw until the at least two adjacent windings anchor and stably fix the wall of the tube-like structure between them by respectively retaining the inner and outer surfaces of the wall between the two adjacent windings; and fixing the means for treating the patient to the screw-device.

20. The method of claim 19, wherein the perforating end is rounded to a point in a conical manner.

21. The method of claim 19, wherein the means for treating the patient comprises at least one of a needle and a catheter, the fixing comprising inserting the at least one needle and catheter into the hollow of the hollow screw and through the wall of the tube-like structure.

22. An anastomosis device configured to be anchored onto a wall of a tube-like structure inside the human body, the anastomosis device comprising:

a hollow screw having a longitudinal axis passing through the hollow of the screw with a plurality of windings coaxially aligned with each other with respect to the longitudinal axis, wherein at least two of the windings of the hollow screw are loose from each other in an axial direction of the hollow screw along the longitudinal axis, the at least two adjacent windings anchor and stably fix the wall of the tube-like structure between them without the need for occluding the tube-like structure by respectively retaining the inner and outer surfaces of the wall between the two adjacent windings, a front winding of said windings has a sharp perforating end, for perforating the wall of the tube-like structure in such a way that passage of the windings of the hollow screw through the wall of the tube-like structure by screwing is enabled to anchor the screw-device to the wall of the tube-like structure, and the two adjacent windings remain coaxially aligned with each other when the screw device is anchored to the wall; and a tube-like member attached to the hollow screw.

23. Surgical screw-device configured to be anchored onto a wall of a tube-like structure inside the human body, the screw-device comprising a hollow screw having a longitudinal axis passing through the hollow of the screw with a plurality of windings coaxially aligned with each other with respect to the longitudinal axis, wherein at least two of the windings of the hollow screw are loose from each other in an axial direction of the hollow screw along the longitudinal axis, the at least two adjacent windings anchor and stably fix the wall of the tube-like structure between them without the need for occluding the tube-like structure by respectively retaining the inner and outer surfaces of the wall between the two adjacent windings, a front winding of said windings has a sharp perforating end rounded to a point in a conical manner, for perforating the wall of the tube-like structure in such a way that passage of the windings of the hollow screw through the wall of the tube-like structure by screwing is enabled to anchor the screw-device to the wall of the tube-like structure, and the two adjacent windings remain coaxially aligned with each other when the screw device is anchored to the wall, wherein the sharp perforating end is rounded to a point for perforating the wall of the tube-like structure, and wherein the sharp perforating end is bent downwardly in an angle of 90 degrees with respect to the other windings.

24. Surgical screw-device configured to be anchored onto a wall of a tube-like structure inside the human body, the screw-device comprising a hollow screw having a longitudinal axis through the hollow of the screw with a plurality of windings coaxially aligned with each other with respect to the longitudinal axis, wherein a front winding of said plurality of windings has a sharp perforating end rounded to a point in a conical manner for perforating the wall of the tube-like structure in such a way that passage of the windings of the hollow screw by screwing is enabled to anchor the screw-device to the wall of the tube-like structure;

the front winding and at least one subsequent winding of the plurality of windings are loose from each other in axial direction of the hollow screw along the longitudinal axis and are configured to anchor and stably fix the wall of the tube-like structure between them without the need for occluding the tube-like structure by respectively retaining the inner and outer surfaces of the wall between two adjacent windings;

the hollow screw is fully open at a rear winding and inwardly from the plurality of windings, such that insertion of a needle or catheter through the screw-device into the wall of the tube-like structure is not obstructed; and the two adjacent windings remain coaxially aligned with each other when the screw device is anchored to the wall, wherein the screw-device further comprises a hollow structure, such as a vessel or a catheter, fixed onto the windings of said hollow screw.

25. Surgical screw-device configured to be anchored onto a wall of a tube-like structure inside the human body, the screw-device comprising a hollow screw having a longitudinal axis through the hollow of the screw with a plurality of windings coaxially aligned with each other with respect to the longitudinal axis, wherein a front winding of said plurality of windings has a sharp perforating end rounded to a point in a conical manner for perforating the wall of the tube-like structure in such a way that passage of the windings of the hollow screw by screwing is enabled to anchor the screw-device to the wall of the tube-like structure;

the front winding and at least one subsequent winding of the plurality of windings are loose from each other in axial direction of the hollow screw along the longitudinal axis and are configured to anchor and stably fix the wall of the tube-like structure between them without the need for occluding the tube-like structure by respectively retaining the inner and outer surfaces of the wall between two adjacent windings;

the hollow screw is fully open at a rear winding and inwardly from the plurality of windings, such that insertion of a needle or catheter through the screw-device into the wall of the tube-like structure is not obstructed; and the two adjacent windings remain coaxially aligned with each other when the screw device is anchored to the wall, wherein the screw-device comprises a hollow tube which is attached to a rear winding of said plurality of windings and is filled with thrombostatic or haemostatic material that functions as a sponge against leakage.

* * * * *